United States Patent [19]

Seaborne et al.

[11] Patent Number: 4,820,533
[45] Date of Patent: * Apr. 11, 1989

[54] EDIBLE BARRIER FOR COMPOSITE FOOD ARTICLES

[75] Inventors: Jonathan Seaborne, Corcoran; David C. Ebgerg, Plymouth, both of Minn.

[73] Assignee: General Mills, Inc., Minneapolis, Minn.

[*] Notice: The portion of the term of this patent subsequent to Apr. 28, 2004 has been disclaimed.

[21] Appl. No.: 117,403

[22] Filed: Nov. 2, 1987

Related U.S. Application Data

[63] Continuation of Ser. No. 803,358, Dec. 2, 1985, abandoned, which is a continuation of Ser. No. 740,797, Jun. 3, 1985, Pat. No. 4,661,359, and a continuation-in-part of Ser. No. 788,178, Oct. 16, 1985, Pat. No. 4,710,228.

[51] Int. Cl.$^4$ ............... A21D 15/08; A23C 19/14; A23G 3/00; B65D 25/08
[52] U.S. Cl. .................................. 426/76; 426/89; 426/90; 426/92; 426/93; 426/94; 426/103; 426/106
[58] Field of Search .......... 426/93, 94, 95, 76, 426/112, 100, 101, 113, 106, 90, 91, 138, 120, 86, 234, 107, 390, 391, 115, 114, 243, 241, 139, 103, 89, 272, 273, 274, 275, 279, 282, 392, 395, 810, 811, 415; 106/200, 218, 219; 427/2, 372.2; 424/33, 34, 92, 103, 101, 102; 260/97; 527/600, 602, 604, 601

[56] References Cited

U.S. PATENT DOCUMENTS

| | | | |
|---|---|---|---|
| 1,484,016 | 2/1924 | Fisher | 426/138 |
| 1,509,194 | 9/1924 | Dresser | 426/76 |
| 1,511,878 | 10/1924 | Gargay | 426/95 |
| 1,529,670 | 3/1925 | Pritchard et al. | 426/94 |
| 1,715,857 | 6/1929 | Meyer | 426/138 |
| 1,810,453 | 6/1931 | Webster et al. | 426/104 |
| 2,077,595 | 4/1937 | Swiss | 426/115 |
| 2,135,808 | 11/1938 | Friedman | 426/95 |
| 2,167,353 | 7/1939 | Frediani | 426/95 |
| 2,600,566 | 6/1952 | Moffett | 426/234 |
| 2,714,070 | 7/1955 | Welch | 426/101 |
| 2,759,826 | 8/1956 | Lindsey | 426/95 |
| 3,042,532 | 7/1962 | Daline | 426/132 |
| 3,186,850 | 6/1965 | Anthony | 426/86 |
| 3,228,776 | 1/1966 | Savage et al. | 426/114 |
| 3,275,448 | 9/1966 | Sommer | 426/120 |
| 3,607,308 | 9/1971 | Dubble | 426/104 |
| 3,741,795 | 6/1973 | Signorino | 426/93 |
| 3,796,813 | 3/1974 | Kurland | 426/132 |
| 3,851,571 | 12/1974 | Nichols | 426/112 |
| 4,039,435 | 8/1977 | Narva | 426/86 |
| 4,061,782 | 12/1977 | Baxter | 426/86 |
| 4,166,208 | 8/1979 | Martel et al. | 426/243 |
| 4,205,091 | 5/1980 | Vanhorne | 426/139 |
| 4,221,291 | 9/1980 | Hunt | 426/115 |
| 4,233,325 | 11/1980 | Slangan et al. | 426/120 |
| 4,390,553 | 6/1983 | Rubenstein | 426/138 |
| 4,472,440 | 9/1984 | Bank | 426/76 |
| 4,596,713 | 6/1986 | Burdette | 426/120 |
| 4,603,051 | 7/1986 | Rubenstein | 426/138 |
| 4,661,359 | 4/1987 | Seaborne et al. | 426/89 |
| 4,710,228 | 12/1987 | Seaborne et al. | 426/89 |

FOREIGN PATENT DOCUMENTS

| | | | |
|---|---|---|---|
| 2612515 | 10/1977 | Fed. Rep. of Germany | 426/86 |
| 476435 | 2/1972 | Japan | 426/138 |
| 555977 | 9/1943 | United Kingdom | 426/115 |

*Primary Examiner*—Steven Weinstein
*Attorney, Agent, or Firm*—John A. O'Toole

[57] ABSTRACT

Disclosed are edible barriers useful in composite food articles to separate one food phase from another which differ in such properties as water activity, protein concentration, etc. The ebible barriers are especially useful in wrapped or packaged food items. The edible barriers comprise an edible laminate which includes an edible support substrate and top and bottom layers of an edible film coating of low moisture permeability.

17 Claims, 4 Drawing Sheets

FIG.10

TABLE 2

LAMINATED EDIBLE BARRIER SHELF-LIFE PERFORMANCE (A)

CEREAL MOISTURE CONTENT (%)

TIME (WEEKS)

| SAMPLE | 0 | 1 | 2 | 3 | 4 | 5 | 6 | 7 | 8 | 9 |
|---|---|---|---|---|---|---|---|---|---|---|
| CONTROL | 3.44 | 5.39 | 12.52 | * | * | * | * | * | * | * |
| A | 3.44 | * | * | * | 5.24 | 4.07 | 4.28 | 5.25 | 5.37 | 6.45 |
| B | 3.44 | * | 4.47 | 4.58 | 3.76 | 5.37 | 5.75 | 4.94 | 6.89 | 5.98 |
| C | 5.17 | * | * | * | 5.94 | 6.15 | 6.57 | 6.05 | 6.09 | 8.49 |
| D | 4.00 | * | * | 5.02 | 5.67 | 6.29 | 6.34 | 8.25 | 8.05 | 7.74 |
| E | 4.26 | 4.36 | 4.84 | * | 4.59 | 5.15 | 4.89 | 5.59 | 5.80 | * |
| F | 4.00 | * | * | * | 5.74 | 5.24 | 5.63 | 6.64 | 6.29 | 7.01 |
| G | 4.00 | * | * | * | 5.75 | 7.01 | 8.23 | 6.84 | 7.64 | 7.72 |

A - TEST CONDITIONS: 36°F INITIAL WATER ACTIVITY GRADIENT 0.8 AW; LOWER COMPARTMENT-YOGURT (0.98 AW); UPPER COMPARTMENT-GRAPE-NUTS® CEREAL (0.18 AW).

* - VALUES NOT DETERMINED

FIG. 11

TABLE 3
LAMINATED EDIBLE BARRIER SHELF-LIFE PERFORMANCE (A)

CEREAL/BARRIER TEXTURE

| SAMPLE | \[TIME (WEEKS)\] | | | | | | | | | |
|---|---|---|---|---|---|---|---|---|---|---|
| | 0 | 1 | 2 | 3 | 4 | 5 | 6 | 7 | 8 | 9 |
| CONTROL | C/C [1,2] | SS/M | M/T | * | * | * | * | * | * | * |
| A | C/C | * | * | * | C/C | C/S | C/S | C/S | C/CR | F/CR |
| B | C/C | * | C/C | C/C | C/C | C/S | S/S | C/S | C/S | C/CR |
| C | C/C | * | * | * | C/C | C/C | C/S | C/T | C/T | S/T |
| D | C/C | * | * | * | C/S | C/S | C/CR | C/M | C/M | S/M |
| E | C/S | C/S | C/S | C/S | C/S | C/S | C/S | C/S | C/S | S/S |
| F | C/C | * | * | * | C/C | C/C | C/C | C/C | C/C | F/S |
| G | C/C | * | * | * | C/C | C/C | C/C | C/C | F/C | F/S |

1 CEREAL TEXTURE/BARRIER TEXTURE

2 TERMONOLOGY: CEREAL; C-CRUNCHY; F-FIRM; S-SOFT; M-SOGGY
BARRIER; C-CRISP; S-SOFT; CR-CRUMBLY; M-SOGGY; T-TOUGH.

A-TEST CONDITIONS: 36°F, INITIAL WATER ACTIVITY GRADIENT 0.8 AW; LOWER COMPARTMENT - YOGURT (0.98 AW); UPPER COMPARTMENT - GRAPE-NUTS ® CEREAL (0.18 AW).

\* - VALUES NOT DETERMINED

EDIBLE BARRIER FOR COMPOSITE FOOD ARTICLES

This is a continuation of U.S. patent application Ser. No. 803,358, filed Dec. 2, 1985, abandoned, entitled Edible Barrier For Composite Food Articles which is a continuation in part application of U.S. Ser. No. 740,797 entitled Edible Coating Compositions Comprising Acid Catalyzed Shellac and Hydroxypropyl Cellulose and Methods of Preparation (filed June 3, 1985), now U.S. Pat. No. 4,661,359 and a continuation in part application of U.S. Ser. No. 788,178 entitled Edible Coating Composition and Method of Preparation (filed Oct. 16, 1985), now U.S. Pat. No. 4,710,228.

BACKGROUND OF THE INVENTION

1. Technical Field

The present invention relates to food products. In particular, the present invention relates to an edible barrier component useful in packaged or wrapped food products.

2. The Prior Art

At present, at least two significant consumer trends influence consumer preference for food products. Consumers increasingly are eating more either away from home or even if at home, away from traditional, sit down full course dinners. Rather, consumers are eating more and more "on the run" whether at home, in work or pleasure activities. The second trend is for consumer preference for food products perceived as being more nutritious than conventional snack items.

Due to these two trends, one particular type of food product enjoying greatly increased consumer popularity is yogurt. Recently, certain styles of yogurt containing partially puffed cereal grains and fruit mixed throughout the yogurt have also been popular. Such products provide relatively crunchy or chewy materials dispersed in a smooth or creamy medium. While popular, such products require specially prepared cereal grains and a fruit in order for the grain and fruit products to maintain their desirable texture while in intimate admixture with the moisture containing yogurt.

Notwithstanding the advantages that such products enjoy over competitive products, it would be desirable to be able to provide products containing two even more widely dissimilar components as a convenience item. Such products, for example, could include yogurt or pudding with ready-to-eat cereal, soup with crackers, cake and ice cream. However, due to the difference in the properties between the two components, physical contact therebetween for extended periods of time result in migration or penetration problems leading to the degradation of the desirable properties of each ingredient.

Among the various potential gradients in such composite food articles, moisture migration remains the most significant problem area. While throughout the remainder of the specification below, particular attention is addressed to the problems of moisture migration and moisture penetration of coating or barrier compositions, the skilled artisan will appreciate that the present invention also finds usefulness in the problems associated with additional migration or penetration problems including oxygen, acidity, color, oil and protein.

The prior art, of course, includes numerous examples of inedible barriers in the form of laminates having moisture impermeable coating (see, for example, U.S. Pat. No. 3,170,568 issued Feb. 23, 1965 to P. H. Carter). Also known are edible containers having an inedible internal moisture barrier (see, U.S. Pat. No. 4,472,440 issued Sept. 18, 1984 to H. M. Bank). U.S. Pat. No. 4,390,553 (issued June 28, 1983 to Rubenstein et al.) discloses an edible food container with a fat coating of its inner surface.

The prior art has included a number of packaging developments to provide two compartment packages to separate dissimilar components until admixture immediately prior to consumption. In particular, U.S. Pat. No. 4,233,325 issued Nov. 11, 1980 to Slangan et al.) disclosed an ice cream package including a compartment for heating syrup. However, the barrier between the syrup and the ice cream is not edible. Thus, the package compartment housing the syrup must be removed entirely and the syrup poured onto the ice cream in the lower compartment. It is possible to make the supporting member of the compartment pierceable or tearable allowing for penetration thereof by, for example, a spoon, the contents of the upper container could then be allowed to fall or drain into the lower compartment. However, such construction suffers from several disadvantages. First, there is a trade-off between support strength of the barrier and the pierceability of the barrier. Second, for barriers which are more readily pierceable, fragments of the barrier material can be intermixed with the food. Not only is such admixture aesthetically unpleasant but consumption of the pieces of ruptured membrane material could possibly result in serious health problems.

Another two compartment package with an edible barrier to separate dissimilar components is disclosed in U.S. Pat. No. 2,714,070 (issued July 26, 1955 to A. E. Welch) where an ice cream cake or cone body is used to separate an upper sauce component from a lower ice cream component in a microwaveable cup. However, such barriers have been found ineffective to prevent moisture migration between the two components over extended storage times even though simple physical separation of the components may be achieved. Also, the ice cream cone material loses its desirable crispness over time due to the moisture migration.

Another edible barrier is disclosed in U.S. Pat. No. 2,600,566 (issued June 17, 1952 to F. W. Moffett) which affords a frozen food package, such as an ice cream package whereby a body of ice cream or frozen dessert and a body of topping or syrup adapted to be liquified upon heating is separated by an edible or other insulating barrier or layer as for instance, a cake-like layer positioned between the ice cream and body of topping material. The cake-like layer acts to keep the syrup or topping hot. Unfortunately, such cake-like barriers, while edible, provide little resistance to moisture migration between the two food components. Thus, at best, such known barriers can be used only with products wherein the components differ only slightly with regard to such important features as water activity or could only be used for frozen foods. Additionally, the cake-like layer provides only modest support strength. Thus, the cake-like barrier could not be used with regard to two-component food products, the major weight fraction of which is a moist food, e.g., yogurt and a minor portion of which is composed of individual pieces of dry, frangible particulate material, e.g., ready-to-eat whole wheat flakes.

Still another problem can exist with edible barriers. If the barriers are fabricated from materials of sufficient strength or rigidity to support heavy amounts of product or which resist breaking or disruption upon ordinary handling, then the barriers may be difficult to pierce when desired or can be broken up into bite sized pieces only with great difficulty.

Accordingly, it is an object of the present invention to provide edible barriers for composite food items.

It is a further object of the present invention to provide edible barriers with enhanced structural support.

Another object of the present invention is to provide edible barriers of enhanced structural support which are resistant to moisture migration.

Still another object of the present invention is to provide strong edible barriers resistant to moisture penetration but which nonetheless are easily breakable by the consumer into bite sized pieces in preparation for consumption of the article.

Another object of the present invention is to provide edible barriers which maintain crispness over extended storage times even when used to segregate high moisture food materials.

A further object of the present invention is to provide composite food articles having two or more phases of different food materials separated with edible barriers which are effective to prevent migration between the different food materials.

It has been surprisingly discovered that the above objectives can be realized and superior edible barriers for composite food products obtained by providing an edible laminate comprising a support substrate being sandwiched between layers of edible films of high moisture impermeability.

SUMMARY OF THE INVENTION

The present invention provides an edible laminated barrier useful in composite food articles to separate food phases differing in properties such as water activity, protein concentration, color and the like. The barriers are highly resistant to moisture migration between the food phases and to degradation by moisture and/or oil, or swelling. The barriers also provide good structural support while nonetheless are readily breakable. The barriers comprise (A) a first layer of an edible support substrate in the form of a sheet or planar form. The substrate can be a cookie, biscuit, wafer or compressed cereal bar, chocolate, compressed nuts, compound chocolates or fat systems. The barrier further essentially comprises (B) a layer of an edible, low-water permeable film overlaying the substrate. The barriers also include (C) a layer of an edible, low-water permeable film underlying the substrate.

The edible water impermeable films comprise shellac based coating resins such as are more fully described below. The overlaying and underlying layers can each range in thickness from about 1 to 5 mils.

The present invention further provides composite food articles comprising a plurality of food materials with an edible barrier separating the food materials and which provides superior resistance to migration between the food materials.

BRIEF DESCRIPTION OF THE DRAWINGS

FIG. 10 is a table presenting analytical tabulated data on the performance of an edible barrier of the present invention in performance testing; and FIG. 11 is a table presenting qualitative tabulated data on the performance of an edible barrier of the present invention in performance testing.

DESCRIPTION OF THE PREFERRED EMBODIMENTS

In one aspect, the present invention relates to edible barriers of superior moisture impermeability useful in packaged composite food articles to separate food phases which differ in water activity, soluble color concentration, acidity, oil concentration and the like. The edible barriers are laminated in construction and comprise a support substrate with over- and underlying coatings of an edible, low-moisture permeability film. Each of these product elements as well as their composition and method of preparation are described in detail below. In another aspect, the present invention provides composite food articles comprising two or more food materials separated by the present edible barriers.

Throughout the specification and claims, percentages and ratios are by weight, and degrees in Fehrenheit, unless otherwise indicated.

Figure 1:
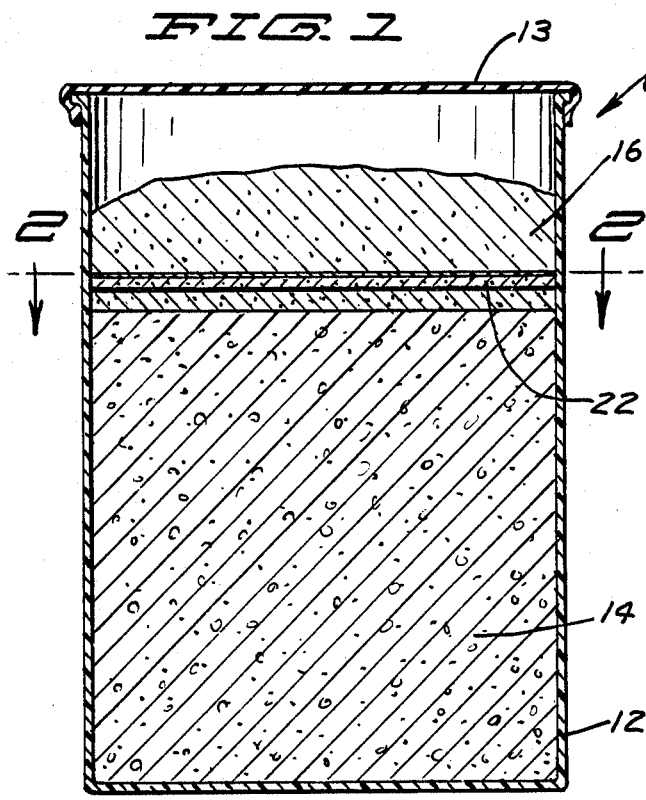
FIG. 1 is a cut away side elevational view of a food package dividing into two compartments by the edible barrier of the present invention and separating a first food from a second food.

Referring now to the drawings, and to FIG. 1 in particular, there is shown an embodiment of the present packaged composite food article which is designated generally by reference numeral 10. As can be seen, the packaged composite food article 10 includes a conventional container or cup 12 which can be an inedible material, plastic, coated paper, and the like or can be fabricated from an edible material, e.g., ice cream cone a.k.a. sugar wafer. The article further includes a conventional top seal closure or lid 13. The article 10 further includes a first or lower food phase or portion 14. The first food region may be any manner of dry or wet food. e.g., yogurt, soup, ice cream or cake whether frozen or liquid. Typically, the lower food portion should be the higher weight fraction of the total food, or the more dense food phase so as to give the article 10 stability from tipping over.

The article 10 further includes an upper or second food portion or phase 16 which differs from the lower food phase 14 in some compositional aspect such as acidity, water activity, or soluble color, protein, oil, and/or oxygen concentration. By virtue of such differences, a gradient would be established were the food phases not effectively sealed against each other which gradient would lead to migration between the two portions or to reaction between components thereof, e.g., Maillard reactions, causing undesirable browning.

The article 10 additionally includes an edible barrier 20 of the present invention. As can be seen, the barrier rests upon the upper surface 22 of the lower food phase 14 and can even be in physical contact therewith.

Figure 2:
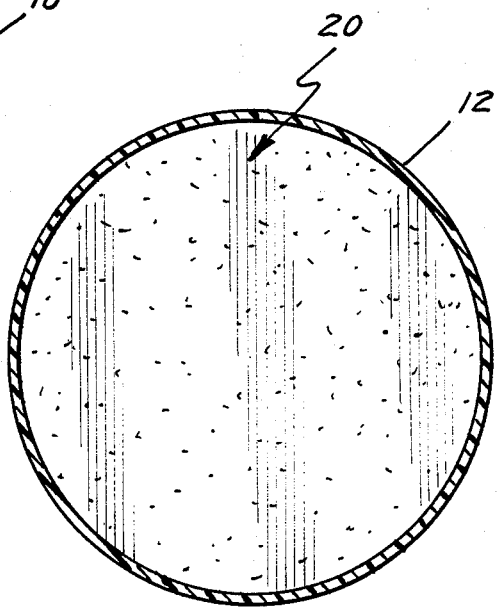
FIG. 2 is a top sectional view taken along lines 2—2 of FIG. 1 showing one embodiment of the present edible laminated barrier.

Referring now briefly to FIG. 2, it can be seen that the edible barrier 20 can be generally circular in construction substantially completely filling the inner diameter of the cup 12. Of course, other shaped containers can also be employed, e.g., square, rectangular, etc. In such embodiments, the present edible barrier 20 is shaped to conform to such alternate cup designs.

Figure 3:
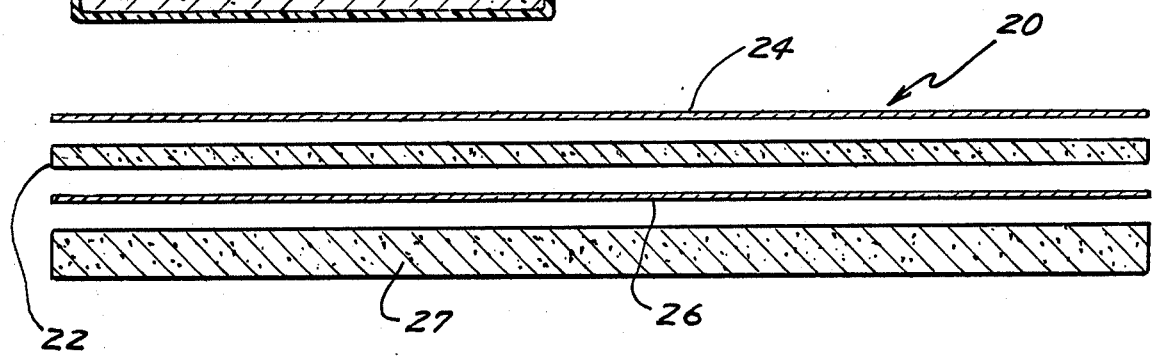
FIG. 3 is an exploded, greatly enlarged cross-sectional view of the laminated, edible barrier taken along lines 3—3 of FIG. 2.

Reference is now made to FIG. 3 which depicts the laminate construction of the present edible barriers 20. The barriers 20 generally include a support of substrate 22. Typically, the substrate 22 is generally planar or is sheet-like in form. The substrate can be formed of any edible material providing models structural support and coherency to support the upper food layer (not shown) and providing a smooth surface. Exemplary materials useful herein include cookies providing such cookies have a smooth, hard surface. The desirability to have a smooth surface as opposed to an open cell or rough surface, e.g., cut layer cake surface, involves the support providing a surface sufficiently smooth to provide a surface to which an even, break-free film or sealant layer (described below) can be applied.

The art is replete with suitable food products having the here described physical features and the skilled artisan will have no difficulty in formulating and fabricating edible substrates suitable for use herein. Among the many substrates useful herein for the substrate 22 are, for example, baked sugar wafers such as used in conventional ice cream cones (see, for example, U.S. Pat. No. 1,876,105, issued Sept. 6, 1932 to W. W. Turnbull and U.S. Pat. No. 1,498,464, issued June 17, 1924 to L. A. Marinelli). Also useful herein for the substrate are bars prepared from compressed cereal fines or nut pieces or powder. Such bars are prepared by merely compressing (e.g., 10–30,000 psi) (730–2200 Kg cm$^{-2}$) particulates with or without excipients or pelletizing agent, e.g., tableting sugars, marketed under the trade name CANTAB by Penick and Ford Limited, Cedar Rapids, Iowa or other fillers and/or magnesium stearates, fats and/or oils and other binding glident and lubricant agents. Both heat tolerant and heat sensitive materials can be employed herein in preparing the substrates or supports. The supports typically are lower in moisture content, e.g., less than 10%, typical of wafers, crackers or biscuits. Other useful support materials include chocolate, cheese, crystalline sugars, peanut brittle, thin candy bars and compounded coatings. Highly preferred materials either remain crunchy or tend to soften slightly upon aging. Less desirable materials like sugar wafers or baked wafers tend to toughen upon aging and become leathery.

Still referring to FIG. 3, it can be seen that the edible barriers 20 additionally essentially comprise an upper or overlaying layer 22 and further essentially comprise a lower or underlying layer 24 each of an edible film material of low moisture permeability. It is important that the film material provide continuous, flexible, moisture impermeable, non-water swelling films. Any edible food film composition providing the above attributes can be used herein, e.g., conventional shellac. Especially suitable compositions, composition preparation and application techniques for use as the film layers are disclosed in U.S. Pat. No. 4,661,359, issued Apr. 28, 1982 by Seaborne et al. entitled EDIBLE COATING COMPOSITIONS COMPRISING ACID CATALYZED SHELLAC AND HYDROXYPROPYL CELLULOSE AND METHOD OF PREPARATION, and U.S. Ser. No. 788,178 filed Oct. 16, 1985, now U.S. Pat. No. 4,710,228, by Seaborne et al. entitled EDIBLE COATING COMPOSITION AND METHOD OF PREPARATION, each of which are incorporated herein by reference. Generally, these coating compositions are polymers of a specially defined, heat cured shellac or copolymers of the shellac with certain other reactants have a reactive acid or hydroxyl moiety. These materials are further described below. Generally, each film layer herein can range from about 0.1 to 5 mil in thickness, preferably 0.5 to 2.0 mil. The films 22 and 24 can be compositionally similar or different so long as the films provide the requisite low moisture impermeability and other properties. Of course, multiple layers can also be used for additional protection.

While good sealant barriers can be prepared employing upper and lower films 24 and 26 as described above, in certain highly preferred embodiments, the edible barriers 20 additionally comprise an edible fat layer 27 in substitution or in addition to the film layer(s). The edible fat layer can be based upon any edible fat or fat based composition, e.g., compound fats which are mixtures of fat and other food solids, typically sugars. Useful, for example herein, are chocolate, whether sweet or semi-sweet, milk or dark chocolate, compound fat, or dairy fat based. Such confectionery coatings are well known in the food art and the skilled artisan will have no problem selecting compositions useful herein. The fat layer, however, is preferably substantially moisture free, i.e., butter and margarine, having moisture contents of about 20%, while useful, are less preferred. The fat layer provides modest additional moisture permeability protection as well as organoleptic improvements. As shown in the drawing, the fat layer is typically substantially thicker than the film layers. Suitable fat layers can range from 0.5 to 3.0 mm (0.019–0.12 inches) in thickness. While less preferred, embodiments of the present barriers can be prepared wherein the film intermediate the support and fat layer is eliminated. Thus, the fat layer while preferably used in combination with the film layers can in less preferred embodiments be used in substitution therefor.

The foregoing description of edible barriers of the present invention contemplate edible barriers which are relatively uniform in thickness although possible with modest mounding when cookies are employed. While useful, such barriers when broken during consumption can break into random and unpredictable size and shape and often break only with difficulty. Indeed, traditional wafer designs, e.g., for ice cream cones, frequently employ raised ribbing to give the wafer added structural support and/or to resist breaking.

Figure 4:
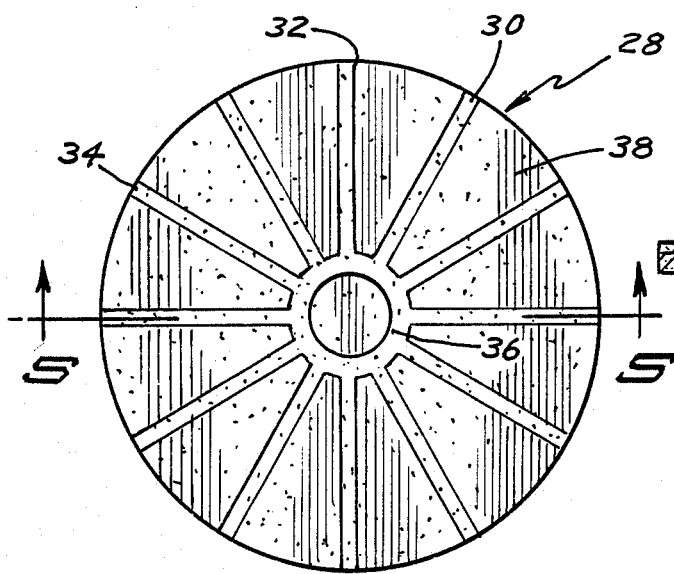
FIG. 4 is a top plan view of another embodiment of a laminated, edible barrier of designed breakability.

Referring now to FIG. 4, there is shown a highly preferred, "designed fracture" substrate 28 embodiment. A designed fracture substrate includes means for fracturing the substrate into pieces of controlled shape and/or size. As shown the substrate 28 is in the form of a controlled disk or round sheet. The substrate is fabricated with a means for controlled fracturing of the substrate such as a plurality of radial grooves or score lines such as 30, 32 and 34. The substrate can also be formed with one or more concentric ring grooves such as 36. Construction of substrates with such grooves and/or score lines provide for controlled and easy fracturing of the disk shaped substrate 28 into wedge or other shaped pieces of roughly similar size and shape.

Figure 5:
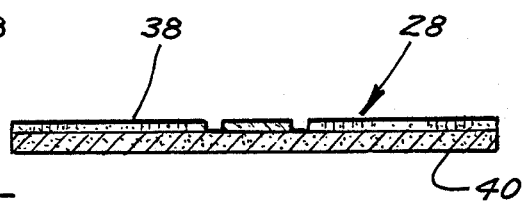
FIG. 5 is an enlarged cross sectional view of the edible barrier taken along lines 5—5 of FIG. 4.

Referring now to FIG. 5, it can be seen that the grooves are relatively shallow. Preferably the grooves are in the top surface 38 of the substrate 28 so that the grooves are more discernable to the consumer so as to aid in the controlled fracture of the substrate 28. The grooves, of course, can be in the lower surface 40 as well, or on both surfaces.

Figure 6:
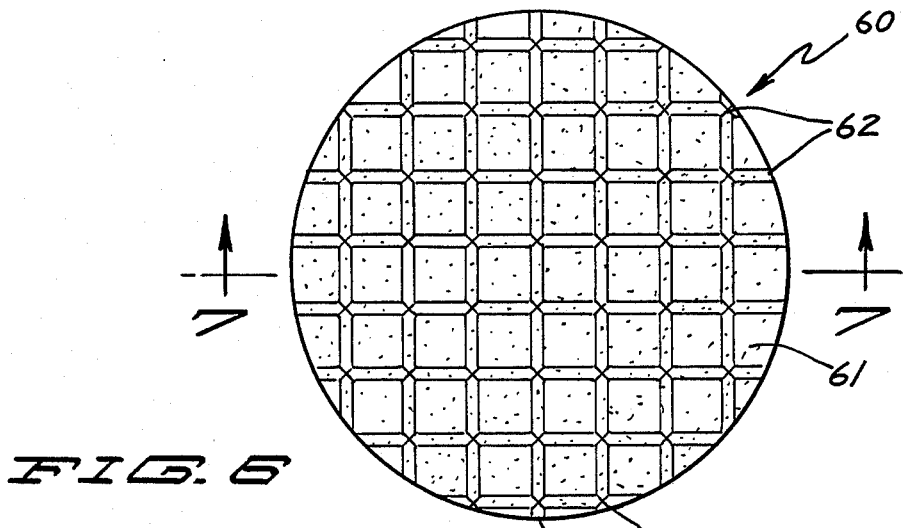
FIG. 6 is a top plan view of another embodiment of an edible barrier substrate designed to provide enhanced structural strength.
Figure 7:
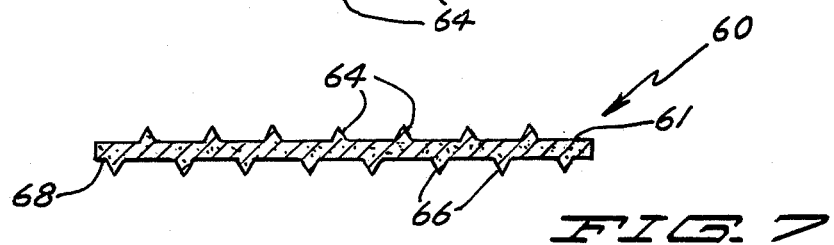
FIG. 7 is a cross sectional view of an edible barrier of enhanced structural strength taken along lines 7—7 of FIG. 6.

Referring now to FIGS. 6 and 7, there is shown still another embodiment of the present substrate wherein a substrate 60 of enhanced structural strength is depicted. As can be seen, the top surface 61 of substrate 60 is provided with a series of vertically and horizontally extending ridges or ribs 62 and 64, respectively. As better seen in FIG. 7, the top layer of ribs 64 in the top surface 61 are offset relative to a series of ribs 66 formed into the bottom surface 68 of the substrate 60. This embodiment finds particular usefulness in supporting larger weights of an upper food material or when larger diameter cups are used.

Figure 8:
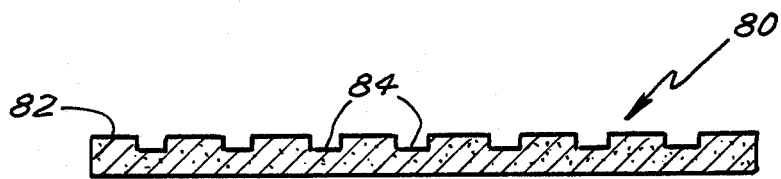
FIG. 8 is a cross sectional view similar to that of FIG. 5 of a second embodiment of an edible barrier substrate of designed breakability.
Figure 9:
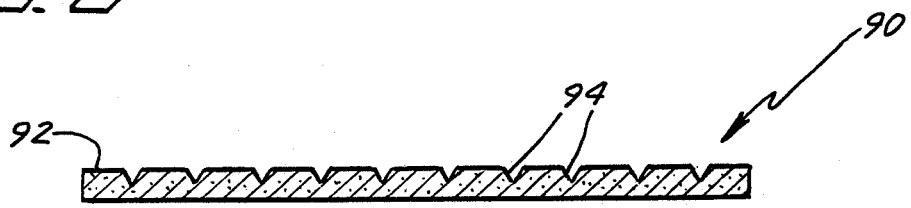
FIG. 9 is a cross sectional view similar to that of FIG. 7 of a third embodiment of an edible barrier substrate of designed breakability.

Referring now briefly to FIGS. 8 and 9, there is shown alternate embodiments of grooves which can be cut into substrates. FIG. 8 shows a substrate 80 having a top surface 82 fabricated with a plurality of square cut shaped grooves 84. Referring now briefly to FIG. 9, there is shown an embodiment of a substrate 90 having a top surface 92 with "V" shaped grooves 94. Of course, the present invention can employ other groove designs and groove shapes.

These substrates as described above are useful herein for use in combination with upper and lower films as are described further below.

In the more highly preferred embodiments, the present coating compositions are prepared using thermoplastic resins essentially comprising the reaction product of shellac with or without a second reactant material having a reactive acid or hydroxyl moiety. As described in detail in the two patent applications referenced above, the second reactant can be an edible member having a reactive acid or hydroxyl moiety such as selected from the group consisting of hydroxpropyl cellulose (HPC), hydroxypropyl methyl cellulose, and mixtures thereof and/or an edible member having a reactive hydroxyl or acid moiety selected from the group consisting of edible sources of phenolics, edible sources of benzaldehyde and its derivatives, acetylated monoglycerides, polyglycerol esters, edible straight chain mono- and di-carboxylic acids and mixtures thereof. Preferred embodiments comprise copolymers of shellac with HPC and any of the edible straight chain mono- and di-carboxylic acids.

Shellac is an essential component of the present coating compositions. Shellac essentially comprises about 25% to 100% of the compositions. Better results in terms of both low moisture permeability and film flexibility are obtained when the shellac comprises about 50% to 99.9% of the composition. Best results are obtained when the shellac comprises about 58% to 99.9% of the coating composition.

Shellacs are commonly treated in various ways to modify its properties. Not all shellacs used in other food applications can be used in this preferred embodiment. It is essential to use only dewaxed, filtered, carbon black decolorized, non-chemically modified or "virgin" shellac. It has been surprisingly found that other refined or bleached shellacs do not possess the reactivity required to cross-link so as to be useful in the present invention. Suitable shellacs are available from commercial suppliers such as Kane International, Larchmont, New York.

In the most highly preferred embodiments, hydroxypropyl cellulose or ("HPC") is the second principal essential component employed in forming the present coating compositions. A closely related material, hydroxypropyl methyl cellulose ("HPMC") can be used in full or partial replacement for HPC. As little as a 0.001:1 weight ratio of HPC has been found to be helpful in adding flexibility and moisture vapor permeability reduction to the shellac film and as much as a 2:1 ratio of HPC has been found to give good moisture vapor impermeability to the shellac film without losing the desirable sealing characteristics of the shellac film. Higher quantities of HPC can produce films which are more sensitive and moisture permeable. For better results, the HPC can comprise about 0.5 to 10% of the compositions.

HPC is a type of cellulose ether. The use of cellulose ethers in food coating compositions is well known. Cellulose ethers, by themselves, however, are generally considered to be unsuitable for coating in view of their brittleness or lack of resiliency, flexibility, and plasticity and, most importantly for some, water solubility. HPC and HPMC are highly water soluble and, undesirably, have a relatively high water permeability. A 2.00 mil film of pure hydroxypropyl cellulose will have a permeability of about $8.73 \times 10^{-7}$ cm$^3$ (STP) cm$^{-2}$ sec$^{-1}$ cmHg$^{-1}$ cm$^{-1}$ and hydroxypropyl methyl cellulose $2.24 \times 10^{-4}$ cm$^3$ (STP) cm$^{-2}$ sec$^{-1}$ cmHg$^{-1}$ cm. Plasticizers which have heretofore been employed in combination with the cellulose ethers are either of the non-edible type or, if edible, have detracted from the thermal stability and barrier properties of the cellulose ether. Additives are generally to be avoided for inclusion herein which have previously been suggested for cellulose ether coating compositions including glycerin, propylene glycol, polyoxyethylene compounds, glycerol monostearate acetylated monoglycerides of fatty acids or acylated fatty glycerides. Thus, preferred for use herein are those films which are substantially free (i.e., contain less than about 0.5% dry weight) of such materials.

The cellulose ethers employed in the coating composition of the present invention are edible cellulose ethers containing between 2.1 and 2.7 ether groups per glucose unit in the cellulose polymer chain. Published information suggests that the hydroxyl propyl substituent groups contain almost entirely secondary hydroxyls and that most of the primary hydroxyl in the cellulose have been substituted. It is the secondary hydroxyls that are the reactive groups remaining. Typical molecular weights for the hydroxyl propyl celluloses range from 60,000 to 1,000,000 and hydroxy propyl methyl celluloses 13,000–120,000.

While the precise phenomenon is not understood, the HPC or HPMC cannot be replaced with equivalent amounts of either methyl or ethyl cellulose. Such substitutions undesirably result in compositions forming films which are brittle and highly water vapor permeable. While not wishing to be bound to the proposed explanation, it is speculated that the hydroxy moieties of HPC are relatively more amenable to forming ester linkages with the shellac than are other types of cellulose ethers.

While effective films can be prepared herein from shellac alone or in combination with HPC, it has been surprisingly discovered that various other components can be added which modestly improve one or more properties of the film, especially water impermeability and flexibility, and film hardness. Each of these classes of materials are organic compounds having reactive hydroxy moieties.

Materials useful herein include mono- and di-carboxylic acids, vanillin, anisaldehyde, cocoa butter, acetylated mono-glycerides, distilled mono-glycerides and polyglycerol fatty acid esters and mixtures thereof. Highly preferred embodiments of the present invention employ minor amounts of certain mono- and di-carboxylic organic acids as reactants in forming the coating compositions. The reactants modestly increase the moisture impermeability of the films. Additionally, the organic acids in part help mask off-flavors associated with shellac.

Especially useful herein are all edible non-substituted mono- and di-carboxylic acids. The skilled artisan will have no problem selecting particular acids for use herein. Preferred reactant materials due to their cost, flavor, availability and favorable affect on film flexibility, water durability and permeability are selected from the group consisting of adipic acid, succinic acid, oleic acid, lauric acid, stearic acid and mixtures thereof. Preferred for use herein are stearic acid, lauric acid and adipic acid.

If employed, these adjuvent materials can be present in the coating compositions in a weight ratio of reactant to combined weight of shellac and HPC ranging from abut 0.0001:1 to 0.25:1, (i.e., at a concentration (dry basis) of 0.01% to 25%). Better results are obtained employing weight ratios of about 0.000:1 to 0.1:1, (i.e., at a concentration of 0.1% to 10%). For best results a ratio of about 0.02:1 is employed.

While the present invention is directed primarily to the superior coating compositions which are copolymers of the present, particularly defined shellac and a second reactant member, the skilled artisan will appreciate that useful coating compositions can be prepared which are monomeric polymers using the selected shellacs described above alone.

Additionally, additives which reduce the growth of microorganisms can be incorporated into the described coating compositions especially when the compositions are to be used for providing protective films on external surfaces.

Such additives or preservatives include sorbic acid, potassium sorbate, methyl p-hydroxybenzoate, sodium benzoate, sodium propionate, and propyl p-hydroxylbenzoate. The addition of even small concentrations of such preservatives results in a marked improvement in reducing or preventing the growth of microorganisms. Adequate protection against the growth of microorganisms is obtained if the concentration of the preservative in the coating constitues about 0.01% to 0.2% by weight of the coating. In addition, suitable anti-oxidants approved for food use can be included in the coating compositions.

The coating compositions are obtained by blending the components and heat curing in a dry state. The heat curing can be practiced as convenient either before or after application to the desired substrate. The blending can be done either by dry blending or by dissolving in a solvent and thereafter removing the solvent.

The most highly preferred method is the pre-application curing embodiment. This method is preferred due to the realization of films which are more highly water-impermeable and resistant to water swelling. The components are first dry blended to form a homogeneous mixture. The order in which the components are admixed is not critical. Thereafter, the dry blend is heated to about 130° C. to 175° C., preferably 138° C. to 150° C. for a period of about 2 to 15 minutes to form the present heat cured coating compositions. Temperatures in excess of 175° C. or the addition of acid catalysts (organic or mineral) cause too rapid and uncontrollable polymerization with the resulting material being insoluble in ethanol and other food approved solvents.

While still molten, the melt or magma is poured into a food grade solvent such as alcohol with agitation. If allowed to cool to solidification, the heat cured shellac based composition is not readily soluble. However, if desired, the cured shellac may be allowed to solidify and then be reheated as convenient for dissolution into the solvent. An acid catalyst is not essential in this embodiment of the method of preparation as in the to-be-described post application technique. In the undiluted form, the shellac itself has sufficient acidic character to initiate polymerization upon simple heating. Within these reaction parameters, it is desired to produce cross-linked shellac having a molecular weight ranging from about 2,000 to 6,000. These pre-application curing methods are particularly uesful when coatings are desired to be applied to heat sensitive materials, e.g., materials of low melting point ingredients and having particular shapes, e.g., chocolate chips. The solution may also be removed to provide resins for the coating compositions.

Another suitable method of preparation is to cure after application to a substrate. In this embodiment, the components are dissolved in a food grade solvent, e.g., ethanol, to form preferably a 10% to 20% solution along with an acid catalyst. Ethanol is the solvent of choice. An edible acid catalyst is essentially employed in this embodiment of forming the present coating compositions. The acid catalyst allows for the accelerated and controlled cross-linking of the shellac. Suitable for use herein are both edible mineral and organic acids. The useful organic acid catalysts herein are distinguished from the organic acid reactants principally by the relatively greater acidity of the acid catalyst materials. Exemplary materials useful herein for the acid catalyst includes citric acid, tartaric acid, phosphoric, tannic, hydrochloric acid, malic acid and mixtures thereof. Preferred for use herein are citric acid and hydrochloric acid.

The acids are used in amounts effective to promote the cross-linking of the shellac. Since the cross-linking step is practiced in a dry state, conventional pH measurements of acidity are inappropriate. However, good results are obtained when the weight ratio of acid catalyst to the combined weight of shellac and HPC ranges in the dry compositions from about 0.001 to 0.1:1. Thus, the reactant solutions from which the pre-heat cured films are prepared can contain about 0.1% to 10%, preferably 0.25% to 5% of the acid catalyst member(s). Best results in terms of optimum hardness and permeability are obtained when the weight ratio ranges from 0.005 to 0.03:1.

The solution is then applied by conventional techniques to a substrate to form a coated substrate and dried. The coated substrate is then heated for 2 to 15 minutes at 130° to 180° C. to cure the coated composition. Slightly longer heating times may be required to bring the temperature to within the above temperature range if the coated substrate has not been completely dried prior to heating. After the heat curing step, the substrate will be covered with the coatings of the present invention. This embodiment is particularly useful for use with substrates which are heat tolerant, e.g., baked goods or container materials.

Of course, additional coat layers can be applied to the substrate if desired to increase further the sealing properties of the coat. The coating obtained with the described coating compositions are strong, highly water and oxygen impermeable, resistant to swelling, flexible and resilient even at freezer temperatures. Even in the form of thin films, continuous, pin-hole-free coatings are readily obtained.

The optimum thickness of a coating employing the present compositions will vary depending on the particular application involved, the degree of protection desired, and the expected storage environment. As a general rule, the coating should have sufficient thickness to assure a continuous coating and give the desired degree of protection, and whether or not it is desirable for the barrier not to be readily apparent. Good sealing protection can be achieved with a coating thickness as thin as 0.25 mil. Greater protection, while nonetheles being organoleptically acceptable, can be provided by films up to about 5 mil thickness. Preferred thicknesses range from about 0.5 to 2 mil.

Thereafter, if employed, a compound fat coating can be applied over or underlying the coated substrate in a conventional manner. Typically, the fat coating is merely heated to melt or plasticize the fat and then is applied to form an even coating. The fat coated substrate is then allowed to cool to room temperature.

To illustrate the advantages of the present coated edible barriers, a series of comparative tests were run. The test included the preparation of two component articles substantially according to FIG. 1. In the samples, the upper food phase comprised a dry food phase, i.e., ready-to-eat cereal, namely, Grape-Nuts TM brand. While the lower food phase comprised a wet food phase, a yogurt, namely Yoplait TM. A variety of samples were prepared differing, except for insignificant differences in amounts or composition of the food phases, only in the composition and structure of the intermediate barrier. Both coated edible barriers of the present invention as well as an uncoated barrier not according to the present invention, for comparison, were tested. Both actual cereal moisture content as analytically determined as well as organoleptic observations were determined. The barriers tested are identified in Table 1 below. Samples A-G are within the scope of the invention and comprise various barriers with shellac coatings alone or in combination with extra fat layers. The results of the analytical testing are given in Table 2 while the results of the qualitative texture testing are given in Table 3 which provides not only the texture observations of the dry cereal material but also of the barrier substrate as well. The results show that after two weeks, articles having an uncoated barrier, i.e, the control, increased in moisture in the dry cereal to over 12% within two weeks. In contrast, none of the articles having barriers of the present invention resulted in such high moisture levels in the dry cereal even after nine weeks of storage. Thus, the comparative testing shows clearly the superiority of the present coated edible barriers in providing protection against moisture penetration when used to separate two food materials differing in moisture content. The qualitative data given in Table 3 further supports the analytical results given in Table 2. Table 2 is a listing of descending textural quality from desirably crunchy to very undesirably tough. The dry cereal of the control became tough after only two weeks storage employing an uncoated edible barrier. In contrast, cereals separated by the present edible barriers maintained desired texture or better texture over extended storage periods. For direct comparison, sample C is substantially similar to the control, except that sample C includes the coating layers of the present invention.

TABLE 1

Sample Identification

Control—Sugar wafer (8.6% sucrose)—baked type, thickness 1.58 mm.

A—A baked cookie—rotary die formulation—sucrose based coated both sides with heat treated shellac 2% by weight and further coated on its high moisture side with a compound fat coating 1 mm in thickness.

B—A baked cookie—rotary die formulation similar to "A" but lactose based, coated as in sample A. Shellac but with its compound coating 1 mm in thickness. Cookie thickness 2.0 mm.

C—Control wafer but coated as in sample A.

D—Compressed synthetic nut-wheat germ based, coated as in sample A. Nut thickness 1.5-2.0 mm.

E—A chocolate disc (Blommer Dark Alamo TM brand chocolate), 1.5 mm thickness coated as in sample A but with the shellac 1% by weight and on its high moisture side only.

F—Hydrox TM cookie (3 in. in diameter) as received from Sunshine Biscuit, Inc., Sayreville, N.J. 08872. Coated as in sample A but with the shellac coating on the high moisture side only at 1% by weight.

G—Vanilla wafer (3 in. in diameter) as received from Sunshine Biscuit, Inc., Sayreville, N.J. 08872. Coated as in sample A, but with the shellac coating on the high moisture side only at 1% by weight.

What is claimed is:

1. An edible laminated barrier useful in composite food articles to separate food phases and resistant to moisture migration, comprising:
   A. an edible, smooth rigid frangible substrate in the form of a sheet;
   B. a layer overlying said substrate; and
   C. a layer underlying said substrate; and wherein each layer is in the form of an edible, continuous, flexible, non-water swelling, low-water vapor permeable film comprising a member selected from the group consisting of
      (1) a composition comprising the heat cured reaction polymer product of
         (A) unbleached, refined, dewaxed, filtered, carbon black decolorized, virgin edible shellac, and
         (B) a first reactant member selected from the group consisting of hydroxypropyl cellulose and hydroxypropyl methyl cellulose and mixtures thereof, wherein the ratio of the reactant member and shellac ranges from 0.001 to 2:1, and wherein the product has an average molecular weight of at least 2,000; and (2) a composition comprising the heat cured reaction polymer product of:

refined, unbleached, dewaxed, filtered, carbon black decolorized virgin, edible shellac wherein the heat cured reaction product has an average molecular weight ranging from about 1,500 to 6,000; and (3) mixtures of composition (1) and composition (2) thereof.

2. The barrier of claim 1 wherein the substrate is selected from the group consisting of smooth hard surface cookies, baked sugar wafers, compressed cereal fines bars, compressed nut powder, cheese, crystalline sugars, peanut brittle, candy bars, compound coatings.

3. The barrier of claim 2 wherein in the heat cured reaction product of subparagraph 1 the reactant member is hydroxypropyl cellulose.

4. The barrier of claim 3 wherein the overlaying and underlying films each range from about 1 to 5 mils in thickness.

5. The barrier of claim 4 additionally comprising a third layer comprising an edible fat.

6. The barrier of claim 5 wherein the substrate is uniform in thickness.

7. The barrier of claim 6 wherein the substrate further includes means for fracturing the substrate into pieces of controlled shape and size.

8. The barrier of claim 7 wherein the means for fracturing includes a plurality of score lines in at least one major surface of the substrate.

9. The barrier of claim 8 wherein the barrier is circular and the score lines include a plurality of radial score lines and at least one concentric ring score line.

10. The barrier of claim 9 wherein the means for fracturing further includes a plurality of score lines on at least two major surfaces of the substrate.

11. The barrier of claim 3 wherein the composition of subparagraph (1) additionally comprises a second reactant comprising an edible organic acid selected from the group consisting of adipic acid, succinic acid, oleic acid, lauric acid, stearic acid and mixtures thereof, and wherein the weight ratio of second reactant to combined weight of shellac and first rectant member range from about 0.0001 to 0.25:1.

12. The barrier of claim 11 wherein the substrate is a smooth hard surface cookie.

13. The barrier of claim 11 wherein the substrate is a baked sugar wafer.

14. The barrier of claim 11 wherein the substrate is a compressed cereal fines bar.

15. The barrier of claim 11 wherein the substrate is a compressed nut powder bar.

16. The barrier of claim 11 additionally comprising an additional layer comprising a moisture free edible fat.

17. The barrier of claim 16 wherein the edible fat layer is a compound fat.

* * * * *